United States Patent [19]
Fink

[11] Patent Number: 5,839,139
[45] Date of Patent: Nov. 24, 1998

[54] HEEL ELEVATOR FOR THE PREVENTION OF HEEL AND FOOT ULCERATIONS

[75] Inventor: John Fink, 2939 Arborry Hill Rd., Richfield, Ohio 44286

[73] Assignee: John Fink, Richfield, Ohio

[21] Appl. No.: 840,029

[22] Filed: Apr. 24, 1997

[51] Int. Cl.⁶ .................................................. A61G 7/075
[52] U.S. Cl. .................... 5/648; 5/650; 5/655.3; 128/822
[58] Field of Search .......................... 5/648, 650, 655.3, 5/657, 900.5, 636, 640, 644, 645; 128/822, DIG. 20

[56] References Cited

U.S. PATENT DOCUMENTS

| | | | |
|---|---|---|---|
| 2,589,155 | 3/1952 | Smith | 5/664 X |
| 2,625,453 | 1/1953 | Lampe et al. | 5/650 |
| 3,424,151 | 1/1969 | Ericson | 128/DIG. 20 |
| 3,462,775 | 8/1969 | Markwitz | 5/648 |
| 5,085,214 | 2/1992 | Barrett | 5/648 X |
| 5,383,843 | 1/1995 | Watson et al. | 602/13 |
| 5,418,991 | 5/1995 | Shiflett | 5/650 |
| 5,497,520 | 3/1996 | Kunz et al. | 5/648 |
| 5,618,263 | 4/1997 | Alivizatos | 128/882 X |

OTHER PUBLICATIONS

Abstracts supplied by the inventor from a novelty search he made.

*Primary Examiner*—Michael F. Trettel
*Attorney, Agent, or Firm*—Roger D. Emerson

[57] ABSTRACT

A heel support for supporting an person's extremity includes an inflatable air bag having three panels, a middle panel and two side panels. An upper surface of the middle panel has a smaller radius of curvature than upper surfaces of the side panels. The panels are connected together in a manner which allows the two side panels to collapse inwardly toward the bottom panel. The side panels fold inwardly toward one another and are secured by an attachment means, preferably hook-and-loop strips.

11 Claims, 3 Drawing Sheets

HEEL ELEVATOR FOR THE PREVENTION OF HEEL AND FOOT ULCERATIONS

BACKGROUND OF THE INVENTION

1. Field of the Invention

This invention relates to a cushion for positioning and supporting the foot or heel of an individual, and more particularly, a device for supporting the Achilles tendon and elevating the heel of a person while they lay for long periods of time in a supine position.

2. Description of the Related Art

Many devices for positioning, supporting or elevating various parts of the body of a person are well known. Pillows and cushions, both inflatable and non-inflatable, are utilized both in homes and institutions, such as hospitals. Institutions have also used other means of support, such as mechanical elevating systems, to elevate a person's extremity, especially with a view of preventing ulcerations.

Prior art devices were somewhat effective although improvements were desirable. For example, pillows tend to be too bulky or not easily adjustable to meet the needs of the comfort level of the individual. Mechanical devices tend to be large in construction, not feasible for in-home use, and are typically expensive. Some prior art devices were difficult to position properly if the user adjusted his position. If the user adjusted his position, for example by turning on his side, the prior art devices did not have the capability to turn with the user. Rather, the leg of the user had to be lifted and then repositioned onto the device.

Another problem not addressed by prior art devices concerned the configuration of the human foot. Because the heel of a user extends outwardly from the centerline of a person's leg, prior art devices that supported a user's foot often allowed the person's heel to touch the surface of the bed. This touching might lead to the circulatory problems addressed by the present invention.

Accordingly, it is the primary object of the present invention to provide for a heel elevator, which elevates the heel and foot of the user comfortably over long periods of time so as to improve circulation and prevent ulcerations.

Another object of the present invention is to provide a heel elevator, which is comfortable to a user in a supine position.

Another object of the present invention is to provide a heel elevator, which is effective in preventing ulcerations and in promoting circulation to the user's extremities.

Another object of the present invention is to provide a heel elevator, which conforms to the indentation behind a person's foot, allowing the heel of the user to hang downwardly without contacting the surface of the bed.

Another object of the present invention is to provide a heel elevator, which supports the heel and foot of the user even when rotating, or turning while in a supine position.

Another object of the present invention is to provide a heel elevator, which is economical in comparison to mechanical devices for supporting the heel and foot of the user.

Still another object of the present invention is to provide a heel elevator, which is easy to operate, maneuver, clean, maintain and repair.

SUMMARY OF THE INVENTION

The present invention includes an article for supporting a portion of a user's body. The article, when assembled, includes a body having first and second side panels and a middle panel. Each of the panels has an upper surface and a lower surface. A radius of curvature of the upper surface of the middle panel is less than a radius of curvature of the first side panel. Likewise, the radius of curvature of the upper surface of the middle panel is less than a radius of curvature of the upper surface of the second side panel. In addition, the radius of curvature of the upper surface of the middle panel is less than a radius of curvature of the lower surface of the middle panel. The radius of curvature of the lower surfaces of the middle, and side panels are approximately infinite.

The article when assembled includes a body having first and second side panels and a middle panel. Each of the panels have an upper surface and a lower surface displaced from their corresponding upper surface. The upper surface of the middle panel is displaced from the lower surface of the middle panel by a maximum distance H1. The upper surface of the first side panel is also displaced from the lower surface of the first side panel by a maximum distance H2 where the distance H1 is greater than the distance H2. Likewise, the upper surface of the second side panel is displaced from the lower surface of the second side panel by a maximum distance H3, where the distance H1 is greater than the distance H3.

The article can be inflatable with air, gel or the like. The middle panel has a volume V1 and the first side panel has a volume of V2, where volume V1 is greater than volume V2. The second side panel has a volume of V3 where volume V1 is greater than volume V3.

The article, when assembled, includes a separator having a first end, a second end, and a width. The separator separates air contained within the middle and first side panels. The panels have a first end and a last end and are heat-sealed. The panels each have a width and a length wherein the separator has a first air gap defined by the front edge of the panel and the first end of the separator. The separator has a second air gap defined by a rear edge of the panel and the second end of the separator. The first air gap is between 0.25 inches (0.635 cm) and 1.50 inches (3.375 cm). The first side panel folds along the separator.

The first side panel is connected to the first end of the middle panel and the second side panel is connected to the second end of the middle panel.

The article further includes connecting means for connecting enclosing means. The enclosing means encloses the heel elevator air bag by connecting the first end of the side panels and the last end of the panels. The connecting means can be a hook-and-loop trip.

DETAILED DESCRIPTION OF THE PREFERRED EMBODIMENT

Figure 1:
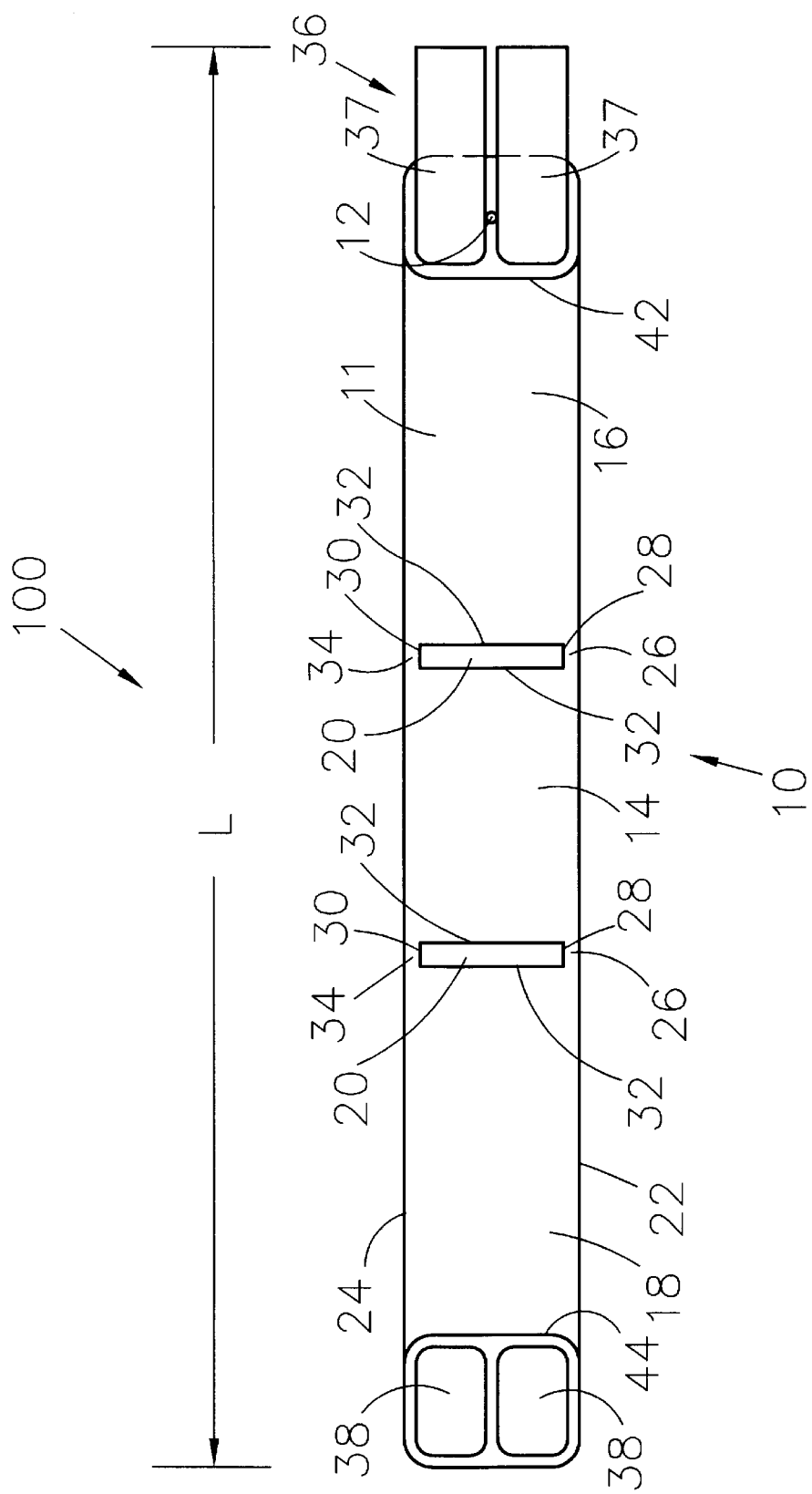
FIG. 1 is a top view of the novel heel elevator.

Referring now to the drawings, which are for purposes of illustrating a preferred embodiment of the invention only, and not for purposes of limiting the invention, FIG. 1 shows the heel elevator uninflated or unfilled, unassembled, and in a flat position. A preferred embodiment of the heel elevator 10 comprises an inflatable or fillable air bag 11 having an inflation valve 12. The valve 12 allows air to be introduced into the air bag 11. A pressurized air source, such as an associated mechanical pump or an associated hand-operated pump (not shown), provides for entry of ambient air into the interior of the air bag 11. The valve 12 also includes a means for preventing discharge of the air. Deflation is also accomplished through the valve 12. Another embodiment of the valve 12 allows air to be introduced from the user's mouth. Such a valve is well known in the field of inflation valves, for example, in inflatable devices to be used in water, such as a beach ball. Another embodiment also allows the air bag 11 to be filled with other mediums such as water, gel, etc.

The inventive heel elevator 10 has a body 100 which is divided up into three panels, a bottom panel 14, a first side panel 16, and a second side panel 18. The panels 14, 16, 18 are separated by separators 20 which, in the preferred embodiment, are heat seals. Also in the preferred embodiment, the separators 20 do not extend across the entire width of the air bag 11. Because the separators 20 do not extend across the entire air bag 11, the air is able to flow from the inflation valve 12 to the panels 14, 16, 18.

Another embodiment of the heel elevator 10 includes an air bag 11, which is separated into separate panels. In this embodiment the heat separators 20 would extend across the entire width of the air bag 11, completely separating the panels 14, 16, 18 from each other. In such case, each of the panels 14, 16, 18 could be inflated by separate inflation valves placed into each of the panels 14, 16, 18.

The width of air gaps 26 is defined by the front edge 22 of air bag 11 and by first end 28 at separator 20. The width of the air gaps 26 must be great enough to allow air to pass freely into panels 14, 16, 18 yet must also be small enough to allow the air bag 11 to fold along edges 32 of separator 20. Second air gap 34 is preferably the same width as first air gap 26 and is defined by second end 30 of separator 20 and rear edge 24 of air bag 11. Elimination or reduction of either air gap 26 or 34 is within the scope of this invention. However, for uniformity sake the preferred air gaps 26 and 34 are equal. In the preferred embodiment, the air gaps 26, 28 are between 0.25 inches and 1.50 inches. The preferred width (X1) of the separators is between 0.25 and 1.50 inches with a preferred width being 0.25 inches.

In the preferred embodiment, the body 100, which is made up of panels 14, 16, 18 and separators 20, is essentially made of vinyl. The separators 20 are preferably manufactured through a heat sealing technique. The design and method of manufacturing the separators 20 enables them to provide flexible joints between flat bottom panel 14 and side panel 16, and middle panel 14 and side panel 18.

FIG. 1 shows air bag 11 having enclosing means 36 secured to, or incorporated within, side panel 16. Enclosing means 36 serves to attach the heel elevator 10 to the leg, foot or ankle of a user. The method of attachment encloses the leg of the user. Enclosing means 36 connects or attaches to side panel 18. FIG. 1 shows enclosing means 36 being hook-and-loop straps 37 which mesh with hook-and-loop elevators 38 that are attached to side panel 18. The hook-and-loop straps 37 and the hook-and-loop elevators 38 are attached to side panels 16, 18 by tape or other securing means. Enclosing means 37 encloses the first panel end 42 and the last panel end 44.

Figure 3:
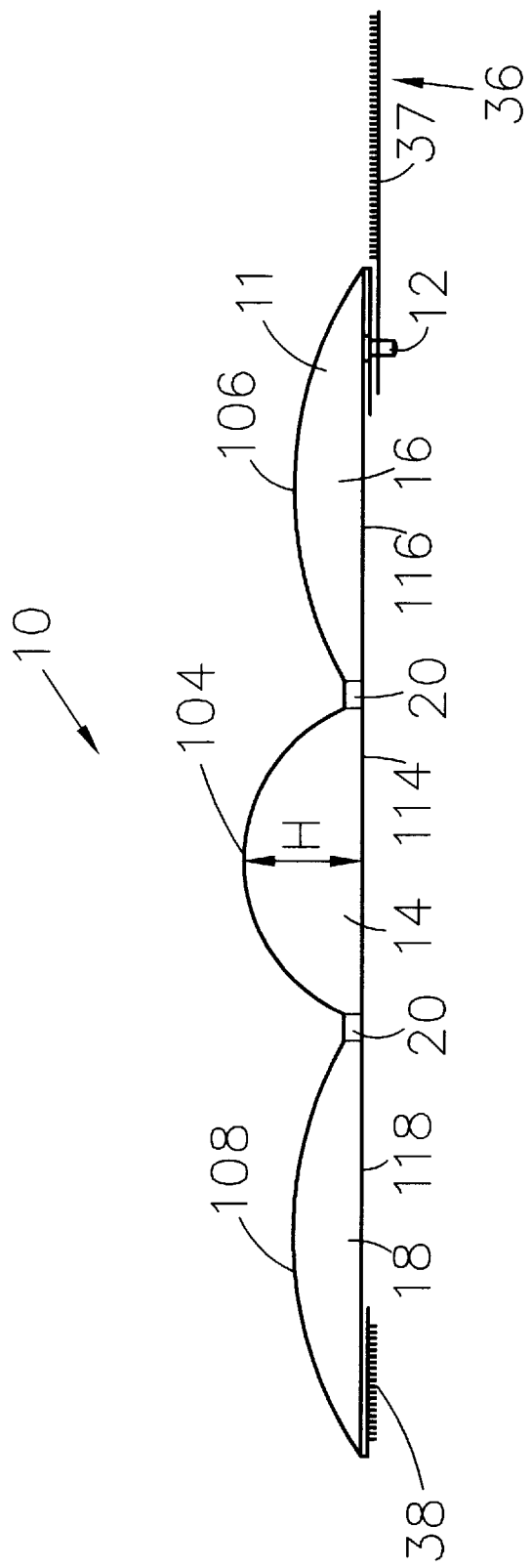
FIG. 3 is a front view of the novel heel elevator shown in an unassembled, uninflated or unfilled, condition.

Referring to FIG. 3, the air supply (not shown) is introduced into valve 12. Air is introduced into the air bag 11 by the user or other means as have been described, thereby allowing air to flow through the valve 12 into the air bag 11. When the air bag 11 has achieved the desired inflation, the air supply is stopped and the inflation valve 12 is closed.

When the user desires less air in the air bag 11, inflation valve 12 is opened. Opening the inflation valve 12 permits the air to escape from the air bag 11 through the valve 12 to the atmosphere. When the desired deflation has been accomplished, the user closes the inflation valve 12, thereby stopping the flow of air from the air bag 11. The air pump, which is not shown, can be mechanical, electrical, or pneumatic.

Referring again to FIG. 3, an important feature of the invention will be described. When viewed in the unassembled, inflated position, as shown in FIG. 3, each panel 14, 16, 18 has an upper surface 104, 106, 108 and a lower surface 114, 116, 118. As is clearly evident from FIG. 3, the length of the upper surface 108, 104, 106 of each of the panels 18, 14, 16 is greater than the length of the lower surface 118, 114, 116 of each of the panels 18, 14, 16. The extra length of the upper surfaces causes the side cross sectional view of each of the panels 18, 14, 16 to be asymmetrical. The radius of curvature of the upper surfaces 108, 104, 106 is smaller than the radius of curvature of the lower surfaces 118, 114, 116 of the panels 18, 14, 16. In fact, in the preferred embodiment, the lower surfaces 118, 114, 116 are planar, yielding an infinite radius of curvature.

In the preferred embodiment, the radius of curvature of the upper surfaces 108, 106, 104 of the side panels 18, 16, are equal while the radius of curvature of the upper surface 104 of the middle panel 14 is smaller. The smaller radius of curvature of the upper surface of the middle panel is important because the foot of the user is to be elevated. Another important aspect of the smaller radius of curvature is that when side panels 18, 16 are assembled a user's ankle is enclosed securely therein.

Figure 2:
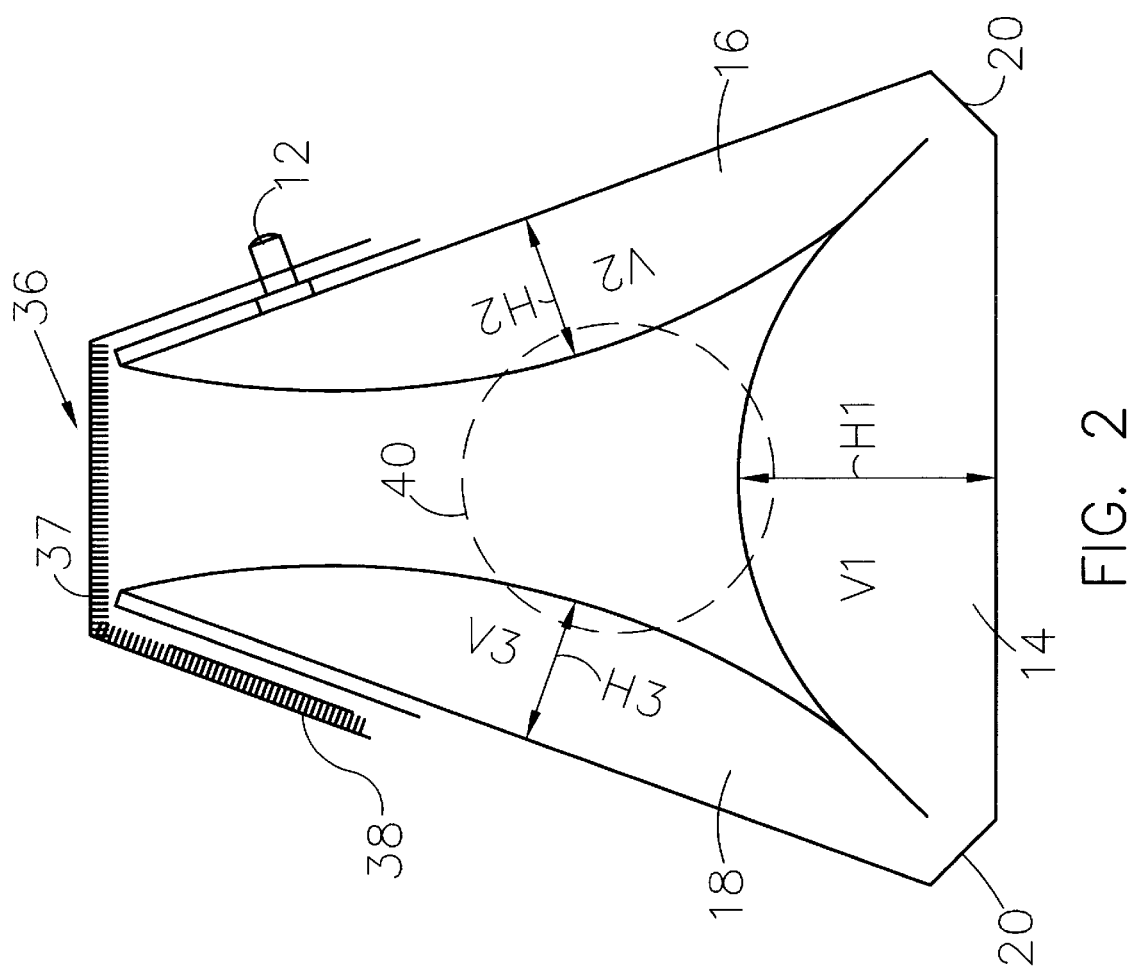
FIG. 2 is a front view of the novel heel elevator shown in an inflated, or filled, and assembled condition, wherein the phantom circle represents the ankle of a user.

Referring now to FIG. 2, the inflatable air bag 11 is shown in an inflated and assembled condition. The phantom circle 40, shown in the center of the air bag 11, depicts the leg of the user. The user is commonly in a supine position lying on a bed and the air bag 11 essentially encloses the users body part, preferably the ankle. In use, the user rests his ankle or, essentially, his Achilles tendon on middle panel 14. The user then secures the heel elevator 10 by using the enclosing means 36, such as a hook-and-loop strap 37, and secures the strap 36 to the hook-and-loop elevator 38. In this embodiment, the user's ankle 40 is enclosed within the air bag 11. The height "H1" of the middle panel 14 primarily depends upon the amount of air introduced into the inflatable air bag 11 which yields volume "V1". However, the volume V1 of air should be enough to allow the heel to be elevated from the surface, which the middle panel 14 rests upon. The heel should be elevated above and not touch the surface for maximum benefit from the invention. The height H1 of the middle panel 14 is preferably greater than the heights "H2" and "H3" of the side panels 16, 18. Similarly, volumes V2, V3 corresponding to panels 16, 18 are preferably less than volume V1 of middle panel 14. Heights H2 and H3 and volumes V2, V3 of side panels 16, 18 are preferably equal in height and volume although they could have unequal heights, volumes and still be within the scope of this invention. Height H1 and volume V1 may also be equal to or less than either heights H2 or H3 and volumes V2 or V3 if the user prefers to have support directed to another area, such as the side of the ankle.

The heel elevator 10, when inflated and assembled, is in essentially a triangular configuration which allows the user, while laying in a supine position, to rotate their bodies while still maintaining proper fit with the inventive heel elevator 10 and while still elevating the injured extremity above the surface of the bed. Therefore, if the user decides to roll over thereby placing his foot in a horizontal position, the air bag 11 still maintains contact with the user's foot and maintain its elevation above the bed surface.

Obviously, modifications and alterations will occur to others upon their reading and understanding of the specification. It is intended by applicant to include all such modifications and alterations insofar as they come within the scope of the appending claims or the equivalents thereof.

Having thus described the invention, it is now claimed:

1. An article for supporting a portion of a user's body, when assembled said article comprising:

a body having first and second side panels and a middle panel, each said panels having an upper surface and a lower surface, a radius of curvature of said upper surface of said middle panel being less than a radius of curvature of said first side panel.

2. The article of claim 1 wherein said radius of curvature of said upper surface of said middle panel is less than a radius of curvature of said upper surface of said second side panel.

3. The article of claim 1 wherein said radius of curvature of said upper surface of said middle panel is less than a radius of curvature of said lower surface of said middle panel.

4. The article of claim 1 wherein said radius of curvature of said lower surface of said middle panel is approximately infinite.

5. The article of claim 1 wherein said radius of curvature of said lower surface of said first side panel is approximately infinite.

6. An article for supporting a portion of a user's body, when disassembled said article comprising:

a body having first and second side panels and a middle panel, each said panels having an upper surface and a lower surface displaced from its corresponding upper surface, said upper surface of said middle panel being displaced from said lower surface of said middle panel by a maximum distance H1, said upper surface of said first side panel being displaced from said lower surface of said first side panel by a maximum distance H2, the distance H1 being greater than the distance H2, said lower surfaces of said panels being planar with respect to one another, said upper surfaces being non-planar with respect to one another.

7. The article of claim 6 wherein the said upper surface of said second side panel being displaced from said lower surface of said second side panel by a maximum distance H3, the distance H1 being greater than the distance H3.

8. The article of claim 1 wherein said article is inflatable.

9. The article of claim 6 wherein said article is inflatable.

10. The article of claim 8 wherein said middle panel has a volume V1 and said first side panel has a volume of V2, said volume V1 being greater than said volume V2.

11. The article of claim 9 wherein said middle panel has a volume V1 and said second side panel has a volume of V3, said volume V1 being greater than said volume V3.

\* \* \* \* \*